US011817220B2

(12) United States Patent
Markram et al.

(10) Patent No.: US 11,817,220 B2
(45) Date of Patent: Nov. 14, 2023

(54) RECONSTRUCTION AND SIMULATION OF NEOCORTICAL MICROCIRCUITRY

(71) Applicant: Ecole Polytechnique Federale De Lausanne (EPFL), Lausanne (CH)

(72) Inventors: Henry Markram, Lausanne (CH); Eilif Benjamin Muller, Preverenges (CH); Sean Lewis Hill, Lausanne (CH); Felix Schuermann, Grens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 342 days.

(21) Appl. No.: 15/728,614

(22) Filed: Oct. 10, 2017

(65) Prior Publication Data
US 2018/0101660 A1    Apr. 12, 2018

Related U.S. Application Data

(60) Provisional application No. 62/405,400, filed on Oct. 7, 2016.

(51) Int. Cl.
*G16H 50/50* (2018.01)
*G16C 20/50* (2019.01)

(52) U.S. Cl.
CPC ............ *G16H 50/50* (2018.01); *G16C 20/50* (2019.02)

(58) Field of Classification Search
None
See application file for complete search history.

(56) References Cited

U.S. PATENT DOCUMENTS

2005/0105463 A1* 5/2005 Deco ................. G06K 9/00536
370/229

OTHER PUBLICATIONS

Tobin et al. Journal of neurophysiology, 2006, vol. 96, No. 4, pp. 2107-2120.*
Roach et al. PLoS Comput Biol 11(8): e1004449, 1-16, 2015.*
Traub et al. J Neurophysiol 93: 2194 -2232, 2005.*
Kasper et al. J Comparative Neurology, 339:459-474, 1994.*
Frazier et al. J Neurophysiol, 1967, 1288-1351.*
Anwar,et al., "An approach to capturing neuron morphological diversity," in Computational Modeling Methods for Neuroscientists (The MIT Press), pp. 211-231, 2009.
Ascoli et al., "Petilla terminology: nomenclature of features of GABAergic interneurons of the cerebral cortex," *Nat Rev Neurosci.*, 9(7):557-568, Jul. 2008.
Beaulieu., "Numerical data on neocortical neurons in adult rat, with special reference to the GABA population," *Brain Res.*, 609:284-292, 1993.

Beierlein et al., "Thalamocortical bursts trigger recurrent activity in neocortical networks: layer 4 as a frequency dependent gate," *J Neurosci.*, 22(22):9885-9894, 2002.
Brunel., "Dynamics of sparsely connected networks of excitatory and inhibitory spiking neurons," *J Comput Neurosci.*, 8:183-208, 2000.
Cauli et al., "Classification of fusiform neocortical interneurons based on unsupervised clustering," *PNAS USA.*, 97(11):6144-6149, May 23, 2000.
Cragg., "The density of synapses and neurones in the motor and visual areas of the cerebral cortex," *J Anat.*, 101(4):639-654, Sep. 1967.
DeFelipe et al., "Microstructure of the neocortex: comparative aspects," *J Neurocytol.*, 31(3-5):299-316, Mar.-Jun. 2002.
Druckmann et al., "A novel multiple objective optimization framework for constraining conductance-based neuron models by experimental data," *Front Neurosci.*, 1:7-18, 2007.
Druckmann et al., "Effective stimuli for constructing reliable neuron models," *PLoS Comput Biol.*, 7(8):e1002133, 2011, 13 pages.
Druckmann et al., "A hierarchical structure of cortical interneuron electrical diversity revealed by automated statistical analysis," *Cereb Cortex.*, 23(12):2994-3006, Dec. 2013.
Fuhrmann et al., "Coding of temporal information by activity-dependent synapses," *J Neurophysiol.*, 87:140-148, Jan. 2002.
Hay et al., "Models of neocortical layer 5b pyramidal cells capturing a wide range of dendritic and perisomatic active properties," *PLoS Comput Biol.*, 7(7):e1002107, 2011, 18 pages.
Hill et al., "Statistical connectivity provides a sufficient foundation for specific functional connectivity in neocortical neural microcircuits," *PNAS USA.*, 109(42):E2885-E2894, 2012.
Hines and Carnevale., "The Neuron simulation environment," *Neural Comput.*, 9:1179-1209, 1997.
Hines et al., "Fully implicit parallel simulation of single neurons," *J Comput Neurosci.*, 25(3):439-448, Dec. 2008.
Hines et al., "Neuron splitting in compute-bound parallel network simulations enables runtime scaling with twice as many processors," *J Comput Neurosci.*, 25:203-210, 2008.
Hines et al., "Comparison of neuronal spike exchange methods on a Blue Gene/P supercomputer," *Front Comput Neurosci.*, 5(49), 2011, 15 pages.
Honey et al., "Network structure of cerebral cortex shapes functional connectivity on multiple time scales," *PNAS USA.*, 104(24):10240-10245, 2007.

(Continued)

*Primary Examiner* — G. Steven Vanni
(74) *Attorney, Agent, or Firm* — Fish & Richardson P.C.

(57) ABSTRACT

Methods, systems, and apparatus, including computer programs encoded on a computer storage medium, for reconstructing and simulating neocortical microcircuitry. In one aspect, a method includes providing a model of neural tissue, the model including different types of neural cells and dynamic synaptic interconnections between the neural cells, changing a parameter in the model; and identifying a change in a computational state of the model of the neural tissue responsive to the change in the parameter. The change in the parameter can, e.g., change behavior of neural cells of at least one type, change interconnectivity between neural cells, or target a location within a volume in the model that interacts with multiple types of neural cells.

16 Claims, 6 Drawing Sheets

(56) References Cited

OTHER PUBLICATIONS

Kasthuri et al., "Saturated Reconstruction of a Volume of Neocortex," *Cell.*, 162(3):648-661, Jul. 30, 2015.

Keller and Carlson., "Neonatal whisker clipping alters intracortical, but not thalamocortical projections, in rat barrel cortex," *J Comp Neural.*, 412:83-94, 1999.

Khazen at al., "Combinatorial expression rules of ion channel genes in juvenile rat (*Rattus norvegicus*) neocortical neurons," *PLoS One.*, 7(4):e34786, Apr. 2012.

Larkum et al., "Dendritic mechanisms underlying the coupling of the dendritic with the axonal action potential initiation zone of adult rat layer 5 pyramidal neurons," *J Physiol.*, 533(2):447-466, Jun. 1, 2001.

Le Be et al., "Morphological, electrophysiological, and synaptic properties of corticocallosal pyramidal cells in the neonatal rat neocortex," *Cereb Cortex.*, 17(9):2204-2213, Sep. 2007.

Lee and Dan, "Neuromodulation of brain states," *Neuron.*, 76:209-222, Oct. 2012.

Lorincz et al., "A distinct class of slow (~ 0.2-2 Hz) intrinsically bursting layer 5 pyramidal neurons determines Up/Down state dynamics in the neocortex," *J Neurosci.*, 35(14):5442-5458, Apr. 8, 2015.

Luczak et al., "Sequential structure of neocortical spontaneous activity in vivo," *PNAS USA.*, 104:347-352, Jan. 2, 2007.

Markram et al., "Interneurons of the neocortical inhibitory system," *Nat Rev Neurosci.*, 5(10):793-807, Oct. 2004.

Meyer et al., "Number and laminar distribution of neurons in a thalamocortical projection column of rat vibrissal cortex.," *Cereb Cortex.*, 20(10):2277-2286, Oct. 2010.

Meyer et al., "Cell type-specific thalamic innervation in a column of rat vibrissal cortex," *Cereb Cortex.*, 20(10):2287-2303, Oct. 2010.

Migliore et al., "Parallel network simulations with Neuron," *J Comput Neurosci.*, 21(2):119-129, Oct. 2006.

Nelson., "Cortical microcircuits: diverse or canonical?" *Neuron.*, 36:19-27, Sep. 26, 2002.

Nevian et al., "Properties of basal dendrites of layer 5 pyramidal neurons: a direct patch-clamp recording study," *Nat Neurosci.*, 10(2):206-214, Feb. 2007.

Okun et al., "Diverse coupling of neurons to populations in sensory cortex," *Nature.*, 521:511-515, 2015.

Perin et al., "A synaptic organizing principle for cortical neuronal groups," *PNAS USA.*, 108(13):5419-5424, 2011.

Peters., "Number of Neurons and Synapses in Primary Visual Cortex," *Cerebral Cortex.*, pp. 267-294, 1987.

Ramaswamy and Markram., "Anatomy and physiology of the thick-tufted layer 5 pyramidal neuron," *Front Cell Neurosci.*, 9(233), 2015, 29 pages.

Ramaswamy et al., "Intrinsic morphological diversity of thick-tufted layer 5 pyramidal neurons ensures robust and invariant properties of in silica synaptic connections," *J Physiol.*, 590(4):737-752, Feb. 15, 2012.

Reimann et al., "An algorithm to predict the connectome of neural microcircuits," *Front Comput Neurosci.*, 9(120), 2015, 18 pages.

Renart et al., "The asynchronous state in cortical circuits," *Science.*, 327:587-590, Jan. 2010.

Sanchez-Vives and McCormick, "Cellular and network mechanisms of rhythmic recurrent activity in neocortex," *Nat Neurosci.*, 3(10):1027-1034, Oct. 2000.

Silberberg., "Polysynaptic subcircuits in the neocortex: spatial and temporal diversity," *Curr Opin Neurobiol.*, 18(3):332-337, Jun. 2008.

Sporns and Kotter., "Motifs in brain networks," *PLoS Biol.*, 2:e369, Oct. 26, 2004.

Spruston., "Pyramidal neurons: dendritic structure and synaptic integration," *Nat Rev Neurosci.*, 9(3):206-221, Mar. 2008.

Toledo-Rodriguez et al., "Correlation maps allow neuronal electrical properties to be predicted from single-cell gene expression profiles in rat neocortex," *Cereb Cortex.*, 14(12):1310-1327, Dec. 2004.

Toledo-Rodriguez et al., "Neuropeptide and calcium-binding protein gene expression profiles predict neuronal anatomical type in the juvenile rat," *J Physiol.*, 567(2):401-413, Sep. 2005.

Van Vreeswijk and Sompolinsky "Chaos in neuronal networks with balanced excitatory and inhibitory activity," *Science.*, 274:1724-1726, 1996.

Wang et al., "Anatomical, physiological, molecular and circuit properties of nest basket cells in the developing somatosensory cortex," *Cereb Cortex.*, 12(4):395-410, Apr. 2002.

Wang et al., "Anatomical, physiological and molecular properties of Martinolli cells in the somatosensory cortex of the juvenile rat," *J Physiol.*, 561:65-90, Nov. 15, 2004.

Zagha and McCormick., "Neural control of brain state," *Curr Opin Neurobiol.*, 29:178-186, 2014.

\* cited by examiner

RECONSTRUCTION AND SIMULATION OF NEOCORTICAL MICROCIRCUITRY

CROSS-REFERENCE TO RELATED APPLICATIONS

This application claims the benefit under 35 U.S.C. § 119(e) of U.S. Patent Application No. 62/405,400, entitled "Reconstruction and Simulation of Neocortical Microcircuitry," filed Oct. 7, 2016, the contents of which are incorporated herein by reference in their entirety.

BACKGROUND

This document relates the reconstruction and simulation of neocortical microcircuitry.

Since Cajal's seminal work on the neocortex (Ramo' n y Cajal, S. (1909, 1911). Histologie du Systeme Nerveux de l'Homme et des Vertebres. L. Azoulay, trans. Maloine, Paris), a vast number of studies have attempted to unravel its multiple levels of anatomical organization (types of neurons, synaptic connections, layering, afferent and efferent projections within and between neocortical regions, etc.) and functional properties (neuronal response characteristics, synaptic responses and plasticity, receptive fields, functional neocortical columns, emergent activity maps, interactions between neocortical regions, etc.). However, there are still large gaps in our knowledge, especially concerning the anatomical and physiological organization of the neocortex at the cellular and synaptic levels. We also still lack an understanding of the cellular and synaptic mechanisms and the role of the different layers in the simplest of behaviors, such as correlated and uncorrelated single-neuron activity and, more generally, synchronous and asynchronous population activity.

For example, although it is known that different types of neurons are connected through synapses with different dynamics and strengths, strategically positioned at different locations on the neurons' dendrites, somata, and axons, the functional significance of this organization remains unclear. Computational approaches that abstract away this level of biological detail have not been able to explain the functional significance of such intricate cellular and synaptic organization. Although future experimental research will undoubtedly advance our knowledge, it is debatable whether experimental mapping alone can provide enough data to answer these questions.

SUMMARY

This document describes the reconstruction and simulation of neocortical microcircuitry using cellular and synaptic organizing principles to algorithmically reconstruct detailed anatomy and physiology from experimental data.

Particular embodiments of the subject matter described herein can be implemented so as to realize one or more of the following advantages. The systems and techniques described herein can yield a digital reconstruction of the microcircuitry that validates against a multitude of experimental datasets not used in the reconstruction. It thus appears to be possible to obtain dense maps of neural microcircuitry without measuring every conceivable biological parameter and point to minimal datasets required, i.e., strategic data. Complementary, albeit sparse, datasets can be integrated to reconcile discrepancies in the literature, at least partially addressing the problem of data quality and reproducibility. The emergent behaviors of the reconstructed microcircuitry reproduce a number of previous in vitro and in vivo findings and provide insights into the design and functioning of neocortical microcircuitry.

The details of one or more embodiments of the subject matter described herein are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
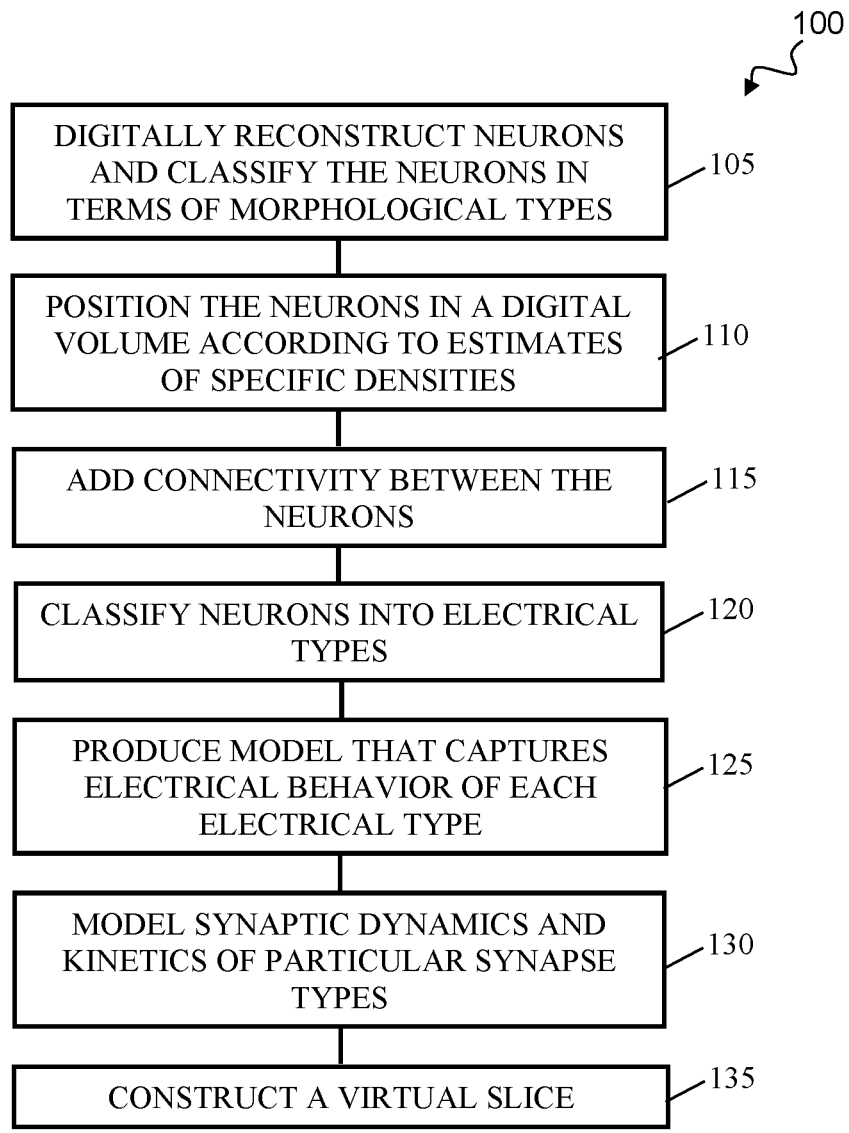
FIG. 1 is a flowchart of a process for reconstruction and simulation of neocortical microcircuitry.

FIG. 1 is a flowchart of a process 100 for reconstruction and simulation of neocortical microcircuitry. Process 100 can yield a digital reconstruction of the microcircuitry that can be used in a variety of different contexts, including identifying the mechanisms of disease or other states, drug discovery, drug development, drug approval, and developing medical devices such as implantable electrodes. In particular, one or more parameters in the digital reconstruction can be changed. A responsive change in the computational state of the digital reconstruction can be identified. The change in the computational state can characterize, e.g., the mechanism of disease or other state, the impact of a drug, or the impact of a medical device.

Process 100 includes digitally reconstructing neurons and classifying the neurons in morphological types at 105. The reconstructed neurons are spatially positioned in a digital volume according to estimates of the specific densities of the morphological types at 110. The specific densities of the morphological types can be estimated based on estimates for a particular type of tissue, e.g., a particular layer of neural tissue in a particular animal. Connectivity between the positioned neurons is added at 115. For example, the connectivity can be added by reconstructing the connectivity based on estimates of the connectivity between neurons in the same particular type of tissue from which specific densities are estimated.

The electrical types of the neurons can be classified at 120. A model that captures electrical behavior of each electrical type can be produced at 125. The synaptic dynamics and kinetics of particular synapse types can be modeled at 130. A virtual slice or other volume of neural tissue can be constructed using the models of the electrical behavior and the synaptic dynamics and kinetics at 135. This virtual volume of neural tissue is thus a reconstruction of the neocortical microcircuitry and can be used to simulate the behavior thereof.

Figure 2:
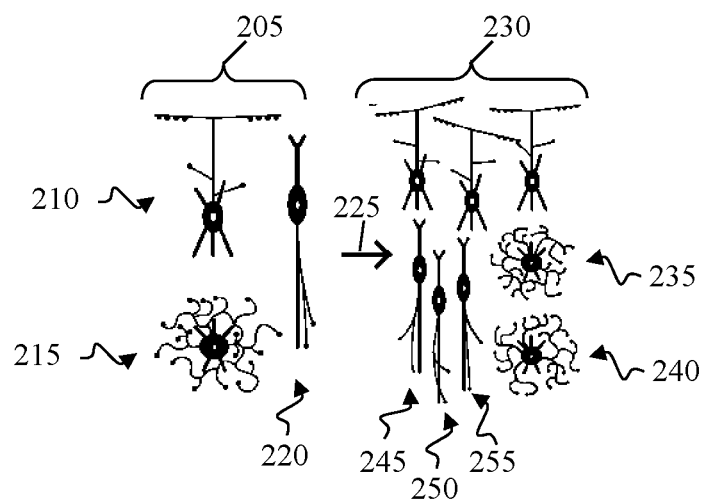
FIG. 2 is a schematic representation of an approach for digitally reconstructing neurons and classifying the neurons in terms of morphological types.

FIG. 2 is a schematic representation of an approach for digitally reconstructing neurons and classifying the neurons in terms of morphological types. The schematically represented approach can be performed, e.g., at 105 in process 100 (FIG. 1).

Initially, a collection 205 of different morphologically-diverse neuron types 210, 215, 220 that are to appear in a digitally reconstructed neocortical microcircuit are identified. Neurons differ, e.g., in terms of their location in the brain, morphology, electrical properties, projections, and the genes and proteins that they express. The combination of these properties implies an immense diversity of neurons. However, in general, classification of neuron morphological types need only consider a subset of these characteristics, e.g., layer, local morphology, and electrophysiology. In some implementations, electrical types (e.g., based on the Petilla convention) can be treated as subtypes of the morphological types.

Table 1 lists various examples of morphological types into which neurons can be classified.

TABLE 1

| MORPHOLOGICAL TYPE | LAYER |
|---|---|
| Descending Axon Cell | I |
| Neurogliaform Cell with dense axonal arborization | I |
| Neurogliaform Cell with slender axonal arborization | I |
| Horizontal Axon Cell | I |
| Large Axon Cell | I |
| Small Axon Cell | I |
| Martinotti Cell | II/III |
| Bitufted Cell | II/III |
| Double Bouquet Cell | II/III |
| Bipolar Cell | II/III |
| Neurogliaform Cell | II/III |
| Large Basket Cell | II/III |
| Nest Basket Cell | II/III |
| Small Basket Cell | II/III |
| Chandelier Cell | II/III |
| Pyramidal Cell | IV |
| Star Pyramidal Cell | IV |
| Spiny Stellate Cell | IV |
| Thick-tufted Pyramidal Cell with a late bifurcating apical tuft | V |
| Thick-tufted Pyramidal Cell with an early bifurcating apical tuft | V |
| Untufted Pyramidal Cell | V |
| Slender-tufted Pyramidal Cell | V |
| Tufted Pyramidal Cell with dendritic tuft terminating in layer 4 | VI |
| Tufted Pyramidal Cell with dendritic tuft terminating in layer 1 | VI |
| Pyramidal Cell with inverted apical-like dendrites | VI |
| Pyramidal Cell with bipolar apical-like dendrites | VI |

Table 1 lists 27 different morphological types into which neurons can be classified. In different implementations, neurons can be classified into different numbers of morphological types. For example, neurons can be classified into 30 or more, 40 or more, 55 or more, or 65 or more different morphological types.

Returning to FIG. 2, the different neuron morphological types can be cloned 225 with statistical variations to enrich the number of exemplars. The cloning yields a collection 230 of different exemplars of morphologically-diverse neuron types 210, 215, 220. For example, exemplars 235, 240 of neuron morphological type 215 and exemplars 245, 250, 255 of neuron morphological type 220 are expressly designated with reference numerals the figure.

In one implementation, greater than 14,000 neurons from all six layers in the somatosensory cortex of P14 male Wistar (Han) rats were recorded and labeled, using patch-clamp electrodes in in vitro slices. Of these neurons, 2,052 were be identified as sufficiently well stained to allow classification into morphological types based on characteristic features of their dendritic and axonal arbors. A subset of these neurons (i.e., 1,009) were digitally reconstructed. The classification can be validated using an objective method based on clustering of characteristic features. An initial pool of digital neuron models used to reconstruct the microcircuitry can thus be provided.

In some implementations, morphological reconstructions for relatively rare morphological types in the microcircuitry can be included. For example, in some cases, relatively rare morphological types can be represented using exemplars of the same morphology from neighboring layers. Some morphologies (e.g., L6 horizontal and sub-plate pyramidal cells) need not be represented. In one implementation, fifty-five or more morphological types (65 or more if layers 2/3 are considered separately or 67 or more if L6_HPC and L6_SPC are also considered) can be distinguished by aggregating morphological reconstructions.

Inhibitory morphological types are generally distinguished by axonal features and excitatory morphological types by dendritic features. In other implementations, a finer separation between morphological types can be introduced. However, finer separation between morphological types limits the number of samples of each morphological type and reduces the reliability of the classification.

In some implementations, the same inhibitory morphological types are present in all layers except layer I, which instead can include a unique set of inhibitory neuron morphological types. In some implementations, pyramidal cell morphologies are varied across layers and also with depth within layer. In some implementations, the number of pyramidal cell types, as defined by their local morphology, increases from upper to lower layers.

In some implementations, several morphological types of interneurons (e.g., LBC and DBC) have axonal arbors that tend to descend to deeper layers when they were in upper layers and that tend to ascend to upper layers when they were in deeper layers. In some implementations, one type of pyramidal cell (L6_IPC) can have inverted axonal arbors.

In some implementations, multiple exemplars obtained from different animals can be used for each morphological type. In some implementations, a repair process can be used to recover arbors cut during slicing. Such a repair process can be validated using in vivo reconstructed neurons.

In some implementations, to generate an even larger pool of unique morphologies, multiple exemplars of each morphological type can be cloned by jittering branch angles and section lengths in the clones. The morphometric properties of the resulting population can be validated against distributions of features obtained from reconstructed neurons. As a result, a dataset of neuronal morphologies that respects biological variability can be established. Processes for repairing and cloning in vitro neuron morphologies and for automated classification of neurons into morphological types can be implemented by data processing apparatus that operate in accordance with machine-readable instructions.

Figure 3:
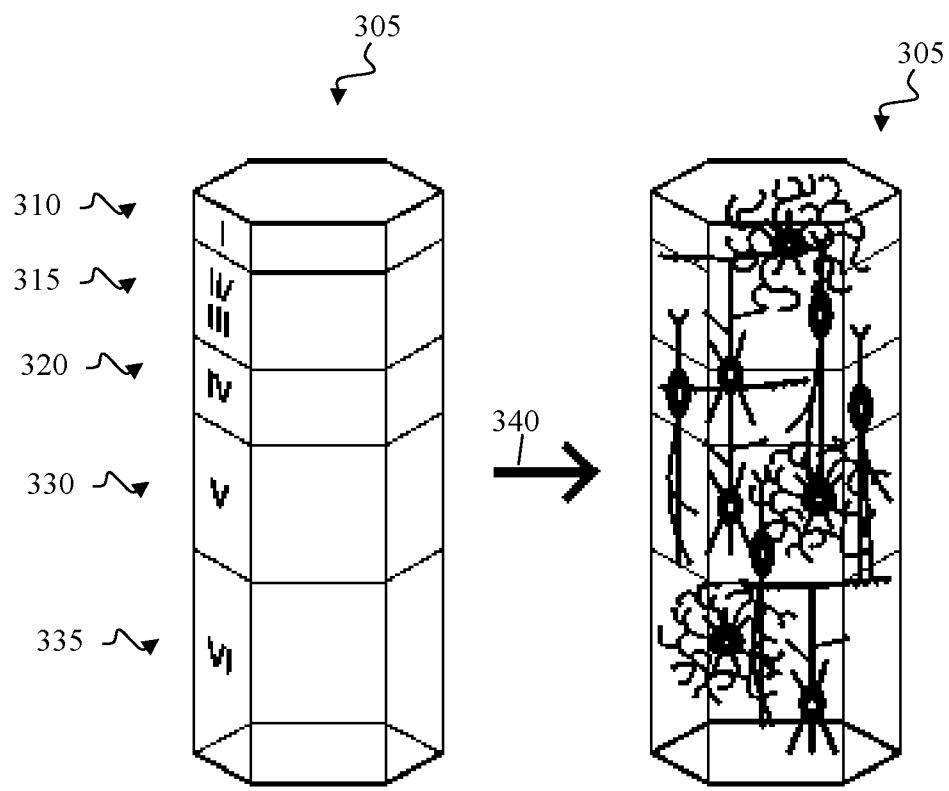
FIG. 3 is a schematic representation of an approach for positioning neurons in a digital volume according to estimates of the specific densities of the neurons.

FIG. 3 is a schematic representation of an approach for positioning neurons in a digital volume according to estimates of the specific densities of the neurons. The schematically represented approach can be performed, e.g., at 110 in process 100 (FIG. 1). In some implementations, the volume of neural tissue can be in excess of 0.1 mm^3, for example, in excess of 0.2 mm^3, Initially, spatial dimensions of the microcircuit 305—including the thicknesses of layer I 310, layer II/III 315, layer IV 320, layer V 330, layer VI 335 are defined. In some implementations, spatial dimensions of the microcircuit 305 can be defined by experimentally measuring the height of the neocortex and heights of each layer in a number of animals to obtain yielding an average overall height. For example, the average overall height can be 2,082±80 microns. Layer thicknesses can be determined experimentally by measuring the location of transitions in cell densities and soma sizes in stained tissue blocks (e.g., NeuN-stained tissue blocks).

Then, individual neurons of different morphological types are assembled 340 in 3-dimensional space according to the frequency of occurrence of each morphological type in the layer, selecting the appropriate morphological type instance that satisfies constraints on the axonal and dendritic distribution for that layer.

For example, fractions of excitatory and inhibitory neurons per layer (E-I fractions) can be established by counting cells stained for DAPI (all cells), NeuN (all neurons), and GABA (all inhibitory neurons) in tissue blocks. In some implementations, the overall excitatory and inhibitory neurons population fractions can be 87%±1% and 13%±1%, respectively, with a trend toward higher fractions of excitatory neurons in deeper layers.

In some implementations, the morphological type composition for the excitatory and all inhibitory neurons in each layer can be obtained from the relative frequencies of each morphological type in an experimental dataset. For example, in some implementations, the same experimental dataset of neurons that were sufficiently well stained to allow classification into morphological types can be used. In some implementations, approximately 50% of inhibitory interneurons can be basket cells (i.e., LBCs and NBCs—predominantly parvalbumin-positive cells; SBCs—predominantly vasoactive intestinal peptide (VIP)-positive cells). In some implementations, Martinotti cells are frequent in all layers except L1. For example, in some implementations, Martinotti cells can be approximately 22% of cells in all layers except L1. In some implementations, bitufted and bipolar cells (i.e., many of the calbindin and calretinin-positive cells) and double bouquet cells (i.e., many of the VIP-positive cells) are both found in layers II-VI. In some implementations, other inhibitory interneuron types are also found in layers II-VI but less frequently.

In some implementations, cells in NeuN-stained tissue blocks can be counted to determine neuronal cell density in different layers. For example, the total mean cell density of can be approximately 100,000 neurons/mm^3 (e.g., 108,662±2,754 neurons/mm^3). In some implementations, neuron densities are highest in layer IV.

In some implementations, the minimum radius of a microcircuit can be defined by placing reconstructed neurons in a cylindrical volume and determining a minimal radius where the density of dendrites saturates at the center. For example, in some implementations, a minimum radius of 200 mm or more (e.g., 210 mm) can be used.

In some implementations, the minimum radius of a microcircuit can be selected to be comparable to the dimensions of the barrels in a barrel cortex, e.g., in the rodent barrel cortex.

In some implementations, the volume of the microcircuit can be defined as a hexagonal prism, with a cross-sectional area greater than or equal to that of a circle with the minimum radius and a height determined by the combined height of the layers. A hexagonal prism volume allows tiling of multiple microcircuits while minimizing edge effects.

The number of each morphological type in each layer and in the whole microcircuit can be calculated using cell densities, morphological type compositions, and circuit dimensions. Inter-individual variation in layer dimensions and neuronal densities can be approximated using digitally reconstructed separate microcircuits corresponding to layer heights and densities measured in multiple animals.

Individual neurons can be positioned after establishing the dimensions of the microcircuit and the number of neurons belonging to each morphological type in each layer. For example, in some implementations, neurons can be arranged in minicolumns at horizontal positions drawn from 2-dimensional Gaussians around the center of each minicolumn. In some implementations, the positions of the neurons along the vertical axis of the minicolumn can be randomly chosen within each layer, using a space-filling algorithm to ensure that somata did not overlap.

Once the positions of the neurons were established, a suitable morphology for each position can be selected. For example, in some implementations, a computer-implemented algorithm can be used to randomly select a suitable morphology for each position from the top 8% of morphologies, scored by their match to typical patterns of arborization within and across layers. In some implementations, the total lengths of axons and dendrites in the average microcircuit can be 350±4 m and 215±3 m, respectively.

In some implementations, the biological accuracy at this stage of the reconstruction can be validated against, e.g., previously unused experimental datasets. For example, in vitro immunohistochemical staining of sections can be compared to in silico immunohistochemical staining of the reconstructed tissue and the correspondence therebetween determined.

Figure 4:
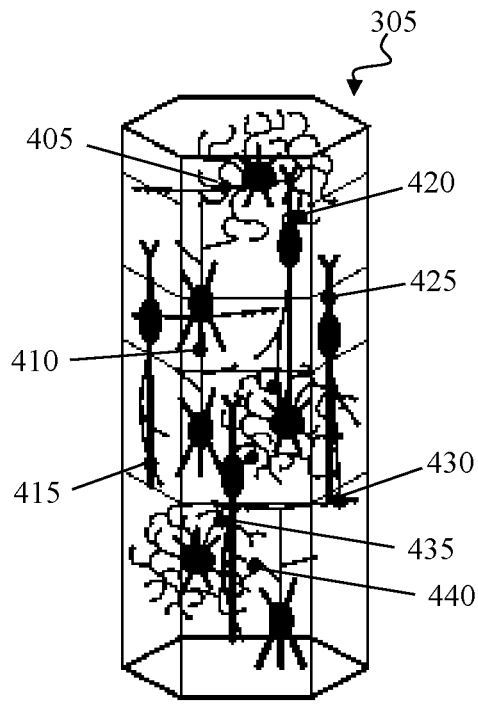
FIG. 4 is a schematic representation of an approach for adding connectivity between neurons that are positioned within a digital volume.

FIG. 4 is a schematic representation of an approach for adding connectivity between neurons that are positioned within a digital volume. The schematically represented approach can be performed, e.g., at 115 in process 100 (FIG. 1). In the illustrated schematic representation, synaptic connectivity rules can be used to reconstruct the number and location of synaptic contacts 405, 410, 415, 420, 435, 430, 435, 440 formed between neurons in the microcircuit. For example, in some implementations, an algorithmic approach can be used to reconstruct the synaptic contacts.

Figure 5:
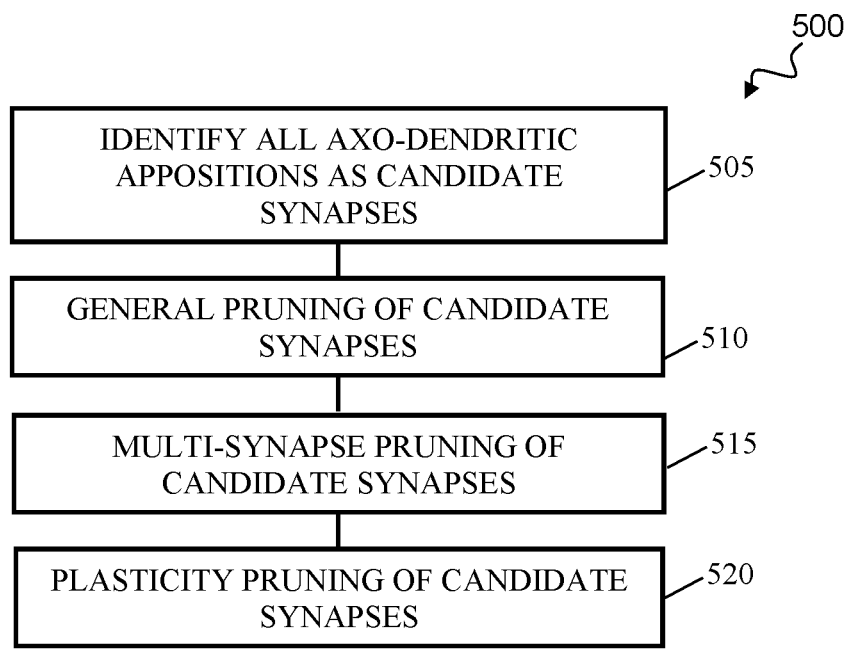
FIG. 5 is a flowchart of a process for adding connectivity between neurons that are positioned within a digital volume.
Figure 6:
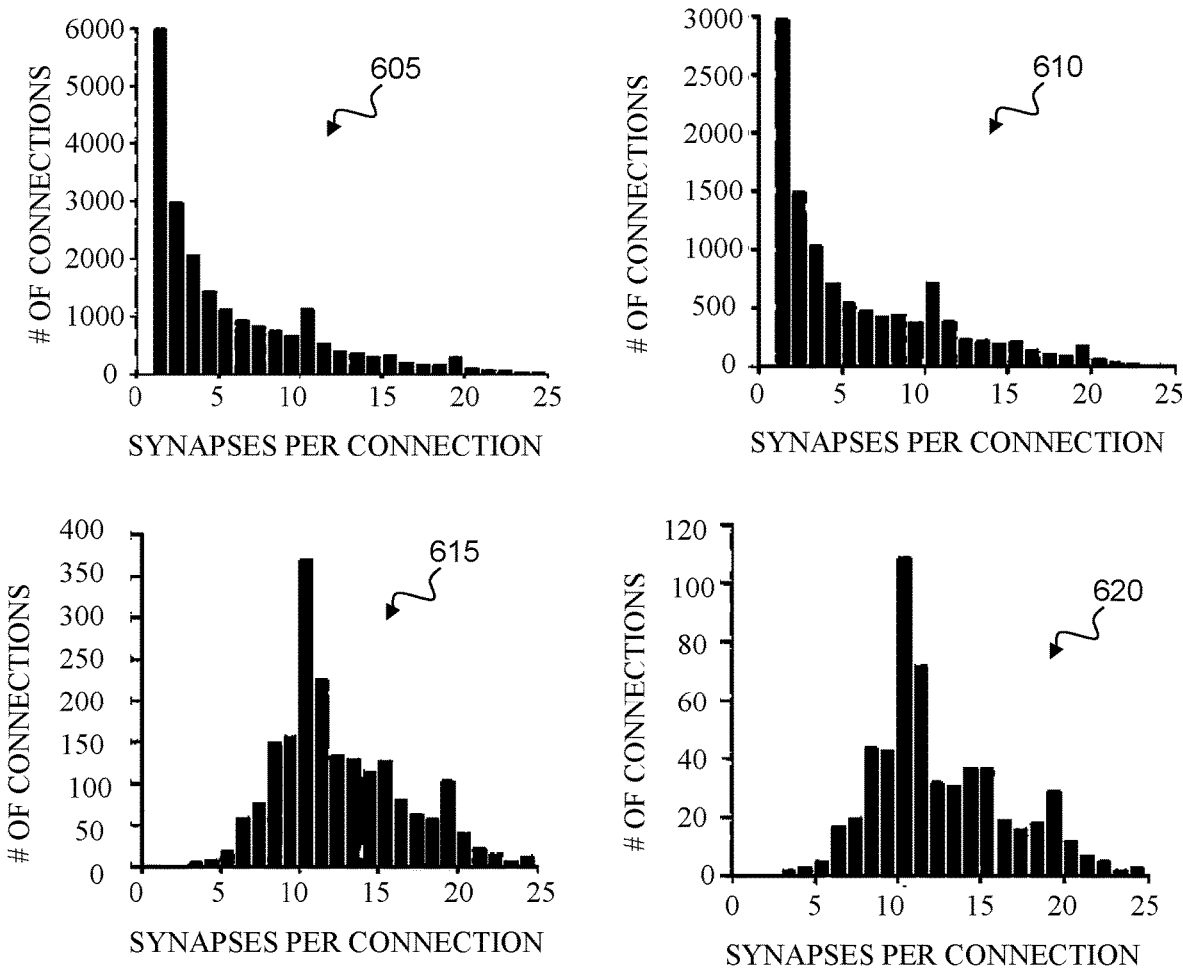
FIG. 6 includes graphs that characterize example distributions of synaptic contacts per connection that can arise during the process of FIG. 5.

FIG. 5 is a flowchart of a process 500 for adding connectivity between neurons that are positioned within a digital volume. FIG. 6 includes graphs 605, 610, 615, 620 that characterize example distributions of synaptic contacts per connection that can arise during process 500.

Process 500 includes identifying all axo-dendritic appositions within a digital volume that has neurons positioned therein as candidate synapses at 505. Graph 605 characterizes an example distribution of candidate synapses per connection after all the axo-dendritic appositions are identified as candidate synapses. As shown, there is a relatively wide distribution of candidate synapses per connection and the probability that any neuron is connected is nearly 100%.

Process 500 also includes a general pruning of the candidate synapses at 510. The general pruning can be, e.g., a random removal of a fraction of the appositions. Graph 610 characterizes an example distribution of candidate synapses per connection after the general pruning. As shown, the distribution of candidate synapses per connection is nearly unchanged but the number of connections is reduced.

Process 500 also includes multi-synapse pruning of the candidate synapses at 515. Multi-synapse pruning remove connections formed by few appositions and shifts the center of the distribution of candidate synapses per connection to the right. The left side of the distribution is removed and short inter-bouton intervals remain. Graph 615 characterizes an example distribution of candidate synapses per connection after multi-synapse pruning.

Process 500 also includes a plasticity pruning of the candidate synapses at 520. Plasticity pruning randomly removes connections and can be tailored so that characteristics of the remaining are in accordance with those characteristics in a particular type of tissue, e.g., a particular layer of neural tissue in a particular animal. For example, inter-bouton-intervals and connection probabilities can be in accordance with those characteristics in a particular type of tissue. Graph 620 characterizes an example distribution of synapses per connection after plasticity pruning.

In some implementations, the synaptic contacts that are reconstructed using process 500 can be used to make predictions of other anatomical characteristics, including those which have not yet been measured experimentally. For example, the numbers of source and target cells and synapses can be predicted using the reconstructed synaptic contacts. In some implementations, the predicted number of synapses/connection is 4.5±0.1 (3.6 for excitatory connections, 13.9 for inhibitory connections). In some implementations, each neuron innervates an average of 255±13 other neurons belonging to 32%±1% of the different morphological types, forming an average of 1,145±75 synapses per neuron present in the microcircuit. In some implementations, as a population, the neurons belonging to a given morphological type innervate 63%±6% of the morphological types in the microcircuit.

In some implementations, reconstructions of a volume of with a radius of 210 mm can yield an average of 638±74 million appositions and 36.7±4.2 million synapses (27.0±2.9 million excitatory and 9.7±1.5 million inhibitory). Taken together, the neurons can form 8.1±0.9 million connections.

In some implementations, the fraction of excitatory synapses increases from layer I to layer VI. In some implementations, the pool of excitatory and inhibitory cells in each layer reveals that recurrent excitation increases with cortical depth while recurrent inhibition is weak in all layers, that descending interlaminar projections are stronger than ascending projections, and that intralaminar inhibition is weakest in layer IV.

In some implementations, afferent fibers from beyond the reconstructed microcircuit of a volume of with a radius of 210 mm (extrinsic synapses) form a further 147±4 million synapses. The total predicted number of synapses in the reconstructed microcircuit is thus 184±6 million, of which only 20%±2% of synapses are formed by neurons belonging to the microcircuit (i.e., intrinsic synapses). In some implementations, a reconstructed microcircuit of a volume of with a radius of 210 mm contains ~41 million mostly en passant afferent fibers.

Figure 7:
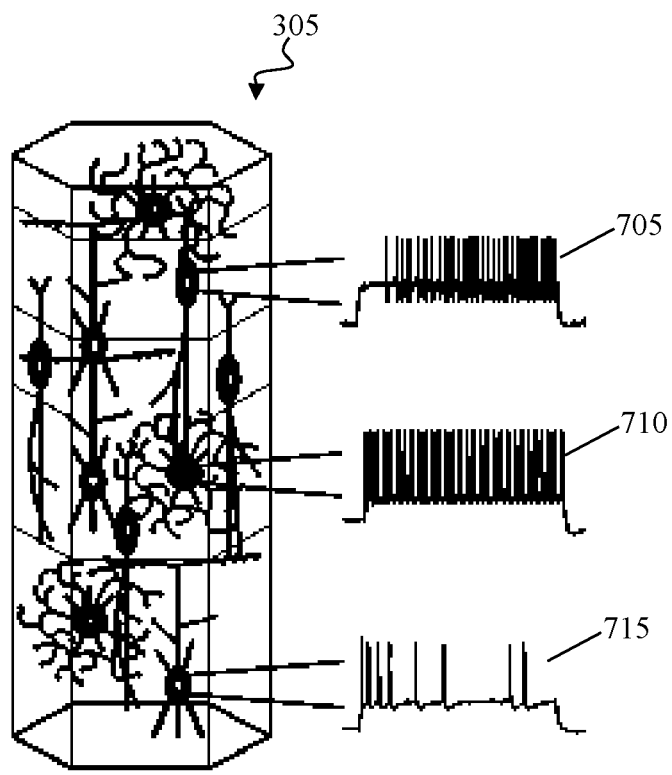
FIG. 7 is a schematic representation of an approach for classify neurons into electrical types.

FIG. 7 is a schematic representation of an approach for classifying neurons into electrical types. The schematically represented approach can be performed, e.g., at 125 in process 100 (FIG. 1), when the neurons are already positioned within a digital volume. In other implementations, neurons can be classified into electrical types prior to positioning within a digital volume, e.g., as they are classified into morphological types.

In the illustrated schematic representation, the electrical types of each morphological type are mapped (e.g., 705, 710, 715) and modeled to account for the observed diversity of subtypes. A battery of stimulation protocols can be applied to neurons from all layers. The responses can be recorded and analyzed. Neurons can be classified using quantified features of the neuronal response to step current pulses, e.g., according to the criteria established by the Petilla convention. In some implementations, stuttering cells can be exceptionally considered as a separate class.

In some implementations, example morphology, ion channel models, and their distribution on soma, dendrites, and axon can be selected. Then, experimental traces from a population of recorded cells can be selected as targets for fitting. Voltage and spiking features can be extracted. To ensure quality, the vector of ion channel conductance densities can be optimized using a multi-objective approach to match the statistics of the extracted biological features in the model. Models with electrical features that do not match the statistics for equivalent features in biological recordings can be discarded. A finite number of electrical type models can result and these electrical type models can be generalized to other example neurons of the same morphological type. A standardized set of measurement protocols can be applied to each model neuron to determine the generalization and the quality of the accepted models can be scored.

In some implementations, in the absence of significant bursting behavior in excitatory morphological types, all excitatory morphological types can be classified as continuous adapting (cAD) neurons. In some implementations, 10 or more electrical types—the majority being inhibitory electrical types—can be identified. For example, in some implementations, 10 inhibitory electrical types and one excitatory electrical type can be identified.

In some implementations, most inhibitory morphological types can express multiple electrical types. Considering both morphological type and electrical type, 200 or more morpho-electrical types (e.g., 207) can be identified.

In some implementations, the dataset of morphologically and electrically classified inhibitory neurons can be used to determine the relative proportion of electrical types for each inhibitory morphological type. In some implementations, the relative proportion is determined in a layer-dependent manner for morphological types with sufficient samples and otherwise in a layer-independent manner. The relative proportions can be combined with neuron densities to calculate the number of neurons for each morpho-electrical type in each layer.

In some implementations, the most common inhibitory electrical type is cAC, followed by cNAC and dNAC, and that stuttering and irregular electrical types (cSTUT, bSTUT, dSTUT, cIR, and bIR) are relatively rare. In some implementations, inhibitory electrical types with regular firing patterns (cAC, bAC, cNAC, bNAC, and dNAC) occur more frequently in superficial layers, whereas electrical types with irregular firing patterns (cSTUT, bSTUT, dSTUT, cIR, bIR) are more common in deep layers.

In some implementations, neuronal physiology can also be reconstructed. For example, in some implementations, a morphologically reconstructed neuron and distributed Hodgkin-Huxley (HH)-type models of known classes of ion channels along the neuronal arbors can be selected. Salient features can be extracted from electrophysiological traces of electrical type responses to step current pulses and data on back-propagating action potentials.

The vector of ion channel conductance densities that best reproduced features such as spike amplitudes and widths, spike frequency, and changes in frequency, and the resulting vector can be computed and transplanted into all neurons belonging to a morphological type. For example, a multi-objective optimization algorithm can perform the computation.

Neurons in the resulting pool of models can be challenged with a separate battery of stimuli not used to fit the vector of ion channel conductances. Ion channel conductances that fell within observed distributions of features can be selected. For example, in some implementations, approximately 40% of models will be acceptable.

In some implementations, neuronal physiology can be reconstructed in an automated workflow to model all morpho-electrical types and a pool of unique neuron models can be generated. In some implementations, the resulting orphoelectrical variation in the ensemble of model neurons is comparable to experimentally-observed biological variation. In some implementations, the resultant electrical behavior is relatively independent of the specific neuron morphologies.

Figure 8:
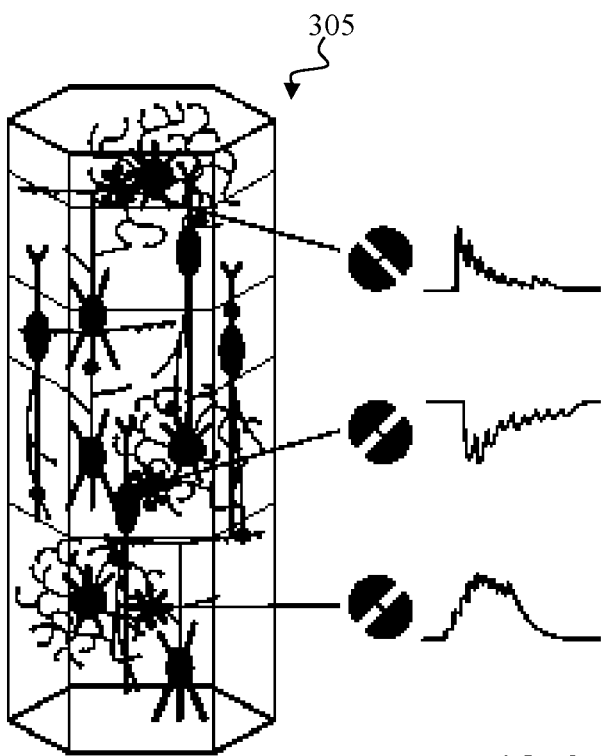
FIG. 8 is a schematic representation of an approach for modelling synaptic dynamics and kinetics of particular synapse types.

FIG. 8 is a schematic representation of an approach for modelling synaptic dynamics and kinetics of particular synapse types. The schematically represented approach can be performed, e.g., at 130 in process 100 (FIG. 1), when the neurons are already positioned within a digital volume.

Synaptic dynamics and kinetics of particular synapse types can be mapped and modelled between pre-post combinations of morpho-electrical types based on rules derived from synaptic physiology. To predict the physiology of the synapses in the reconstruction, paired-recording data and reported synaptic properties (e.g., conductances, postsynaptic potentials [EPSPs/IPSPs], latencies, rise and decay times, failures, release probabilities) can be integrated into the reconstruction.

For example, neocortical synapses display known forms of short-term dynamics, which we used to classify synaptic connections as facilitating (E1 and I1), depressing (E2 and I2), or pseudo-linear (E3 and I3) synaptic types. The synaptic types of specific connections can be determined from the combination of their pre- and postsynaptic morpho-electrical types.

Since physiological characterization of all unique morpho-electrical type-to-morpho-electrical type connections is difficult, synaptic types in which experimental data were missing can be specified using one or more rules. For example, in some implementations, synaptic types classes of connections can be predicted using one or more of the following:

(1) pyramidal-to-pyramidal connections are always depressing (E2);

(2) pyramidal-to-interneuron connections are also depressing (E2), except for connections onto Martinotti, bitufted and other interneuron types displaying spike frequency accommodation, which are facilitating (E1);

(3) facilitation from inhibitory neurons is around two times stronger than from excitatory neurons;

(4) synaptic dynamics are preserved across layers for all morpho-electrical type-specific connections; and (5) any remaining connections belong to the most common synaptic type (type 2; E2 or I2).

In some implementations, parameters for the synaptic dynamics of individual synapses can be drawn from experimental distributions. In some implementations, a complete map of synaptic dynamics can be generated. Stochasticity of synaptic transmission can also be modeled.

In some implementations, the conductances to all specific connections where data were missing can be estimated based on an average corrected synaptic conductances for broader classes of synaptic connections (e.g., E-E, E-I, I-I, I-E).

In some implementations, unique quantal synaptic conductances for individual synapses were drawn from truncated normal distributions around mean synaptic conductances or all morphological type-to-morphological type connections.

In some implementations, the reconstruction now allows in silico retrograde staining experiments for any neuron in the microcircuit, providing a detailed view of its presynaptic neurons and their synapses. In silico anterograde staining for postsynaptic neurons is also possible.

In some implementations, the morphological-, electrical-, and synaptic-types of inputs to any particular neuron are different from those of its outputs (i.e., inputs and outputs were highly asymmetrical). In some implementations, the average total synaptic conductance for single neurons was approximately 1000 nS (approximately 750 nS excitatory and approximately 250 nS inhibitory conductance. In some implementations, the predicted average quantal conductance was 0.85±0.44 nS for excitatory synapses (corresponding to approximately 150 AMPA and approximately 20 NMDA receptors) and 0.84±0.29 nS for inhibitory synapses (corresponding to approximately 40 GABAA receptors). In some implementations, the average failure rate across all morphological type-to-morphological type connections was 11.1%±14.1%.

Figure 9:
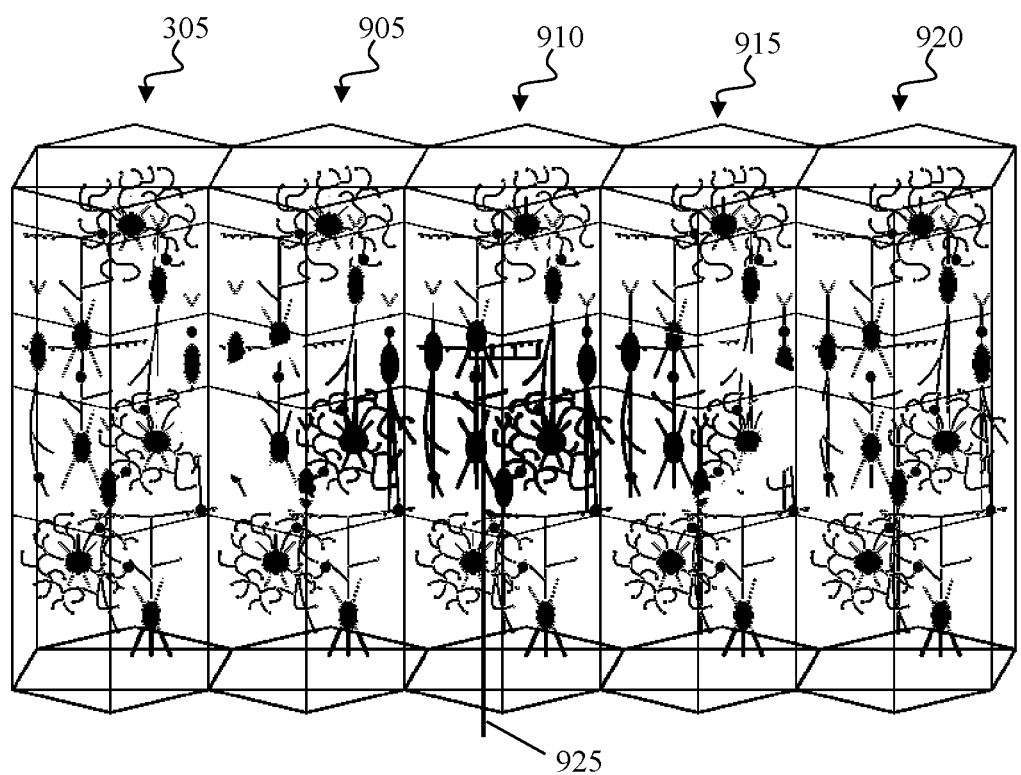
FIG. 9 is a schematic representation of an approach for constructing a virtual slice of neural tissue.

FIG. 9 is a schematic representation of an approach for constructing a virtual slice of neural tissue. The schematically represented approach can be performed, e.g., at 135 in process 100 (FIG. 1). In the approach, the previous steps can be repeatedly applied to reconstruct defined circuit volumes 305, 905, 910, 915, 920 that are assembled to form a virtual slice for in silico experiments. Further, fibers 925 and corresponding synapses can be added for stimulation experiments.

Such a virtual slice of neural tissue (or a portion thereof) can be used as a model of neural tissue. One or more parameter of the virtual slice of neural tissue can be changed, and a change in a computational state of the model of the neural tissue responsive to the change in the parameter can be identified. For example, the change in the parameter can change the behavior of neural cells of at least one morphological-, electrical-, and/or synaptic type, the interconnectivity between neural cells, or a location within a volume in the model that interacts with multiple types of neural cells.

In some implementations, the parameter is a biophysical parameter and the change in the parameter in the model is concordant with a real-world change to the biophysical parameter of neural tissue.

For example, in some implementations, the change in the parameter simulates tonic depolarization and spontaneous activity results in the virtual slice of neural tissue. For example, neurons belonging to all morphological types can become active and the network can exhibit spontaneous slow oscillatory population bursts, initiated in layer V, spreading down to layer VI, and then up to layer IV and layer 2/3 with secondary bursts spreading back to layer 6. In some implementations, despite the apparent global synchrony, different morphological types can generate diverse patterns of spiking.

As another example, in some implementations, the change in the parameter simulates a change in calcium ion Ca2+ concentration. For example, a change in calcium ion Ca2+ concentration can be simulated by modulating the probability of neurotransmitter release consistently with experimental data for the specific sensitivities of different synaptic types to changes in calcium ion Ca2+ concentration. At low calcium ion Ca2+ concentrations, slow oscillatory bursting disappeared and the neuronal activity became asynchronous and irregular.

As another example, in some implementations, parameters that simulate both tonic depolarization and a change in calcium ion Ca2+ concentration can be simulated. A spectrum of network states ranging from one extreme, where neuronal activity was largely synchronous, to another, where it was largely asynchronous can result.

As yet another example, in some implementations, in silico knockout experiments can be performed. In such experiments, the activity of different features of the virtual slice of neural tissue is blocked. The features can include, e.g., different layers, different neurons, and different connections. The responsive change in the computational state of the virtual slice of neural tissue can be identified. For example, in some implementations, blocking activity in the upper layers can tend to shift the virtual slice of neural tissue toward the synchronous state, while blocking the deeper layers can have the opposite effect. As another example, in some implementations, blocking soma-targeting basket cells can produce a stronger shift toward the synchronous state than blocking other interneurons, whereas blocking pyramidal cells can cause a shift toward the asynchronous state. As another example, in some implementations, blocking associated inhibitory and excitatory connections can cause corresponding differential effects.

As yet another example, a parameter that simulates the presence of an electrode or neural input (e.g., from the thalamus) can changed. For example, in some implementations, input from the thalamus to the central microcircuit can be approximated using data for the number of incoming fibers, bouton density profiles, and the numbers of synapses per connection (to layer IV) for the ventral posteromedial (VPM) thalamic input to the barrel region of somatosensory cortex. For example, one fiber centered in each minicolumn with a horizontal spread can be simulated. Layer-by-layer bouton density profiles, experimental measurements of the mean number of synapses per thalamic connection in layer IV, and the multi-synapse principle can be used to predict the synapses that each thalamic fiber forms onto different morphological types. The reconstruction can reproduce the number of synapses formed and in some implementations can include an average of approximately 12 synapses on layer IV pyramidal neurons. For example, each thalamic fiber can innervate 903±66 neurons (775±57 excitatory and 83±11 inhibitory neurons) with an average of 8.1±4.2 synapses/connection. In some implementations, thalamic fibers can form approximately 1% of synapses across all layers.

As yet another example, in some implementations, a parameter that simulates the presence of a pharmaceutical or other biologically active composition can be changed. For example, a biologically active composition can change, e.g., the characteristics of ion channels, synapses, and/or other features of the virtual slice of neural tissue. Changes in the computational state of the virtual slice of neural tissue that result from the presence of the biologically active composition can be identified.

As yet another example, in some implementations, a parameter that simulates the presence of a disease state can be changed. For example, a disease state can change, e.g., the characteristics of ion channels, synapses, neurotransmitter concentration, receptor concentration or activity, and/or other features of the virtual slice of neural tissue. Changes in the computational state of the virtual slice of neural tissue that result from the disease state can be identified.

One or more non-transitory computer readable storage media can store instructions executable by one or more data processing apparatus, wherein upon such execution the instructions cause the data processing apparatus to providing the model of neural tissue as described above, receiving input changing a parameter in the model, and outputting information identifying the change in the computational state. A system can include one or more data processing apparatus and one or more or such non-transitory computer readable storage media.

Further, embodiments of the subject matter and the operations described herein can be implemented in digital electronic circuitry, or in computer software, firmware, or hardware, including the structures disclosed herein and their structural equivalents, or in combinations of one or more of them. Embodiments of the subject matter described herein can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The specific implementation details described herein should not be construed as limitations on the scope of any inventions or of what may be claimed, but rather as descriptions of features specific to particular embodiments of particular inventions. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described herein should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A simulation method implemented by a data processing apparatus, the method comprising:
   providing a virtual volume of neural tissue as a reconstruction of neocortical microcircuitry, comprising providing a computer-implemented model of the neural tissue, the model including different types of neural cells and dynamic synaptic interconnections between the neural cells;
   performing in silico knockout experiments on the virtual volume of neural tissue to simulate functioning of the neocortical microcircuitry, comprising:
   receiving multiple user inputs, wherein each user input changes a respective morphological characteristic of at least one type of neural cell in the computer-implemented model, wherein the change in the respective morphological characteristic
      i) blocks activity in a respective layer of the neural tissue to changes a behavior of neural cells in the neural tissue, or
      ii) blocks respective types of connections in the neural tissue to changes the interconnectivity between neural cells in the neural tissue; and
   identifying changes in a synchronicity of neuronal activity in the computer-implemented model of the neural tissue responsive to the changes in the morphological characteristics, comprising identifying shifts of the neural tissue towards a synchronous state or an asynchronous state in response to the changes in the morphological characteristics; and
   determining a mechanism of a disease state or an impact of a drug based on the changes in the synchronicity of the neuronal activity.

2. The method of claim 1, wherein the morphological characteristic is a biophysical parameter and the change in the morphological characteristic in the computer-implemented model is concordant with a real-world change.

3. The method of claim 1, wherein the morphological characteristic is a local change to neural cells of a first type that leaves neural cells of all other types unchanged.

4. The method of claim 1, wherein the morphological characteristic is a characteristic of a dynamic synaptic interconnection between neural cells.

5. The method of claim 1, wherein:
the method is a method for drug discovery, drug development, or drug approval; and
identifying the change in the synchronicity of the neuronal activity in the computer-implemented model of the neural tissue characterizes an impact of a drug on the synchronicity of the neuronal activity in the computer-implemented model of the neural tissue.

6. The method of claim 1, wherein:
the method is a method for investigating a disease state; and
the change in the synchronicity of the neuronal activity in the computer-implemented model of the neural tissue characterizes the disease state.

7. The method of claim 1, wherein the change in the synchronicity of the neuronal activity in the computer-implemented model of the neural tissue is an emergent property of the computer-implemented model of the neural tissue.

8. The method of claim 7, wherein identifying the change in the synchronicity of the neuronal activity in the computer-implemented model comprises discovering a previously unknown change in the synchronicity of the neuronal activity in the computer-implemented model.

9. The method of claim 1, wherein the computer-implemented model of the neural tissue is a model of mammalian neural tissue.

10. The method of claim 1, wherein the computer-implemented model of the neural tissue is an algorithmically reconstructed model of anatomy and physiology of the neural tissue.

11. The method of claim 1, wherein the computer-implemented model models a volume of neural tissue in excess of 0.1 mm^3.

12. The method of claim 1, wherein the computer-implemented model comprises:
model neurons digitally reconstructed from neurons of the neural tissue;
positions of the model neurons in a digital volume based on estimates of specific densities of the neurons in the neural tissue; and
connectivity between the model neurons reconstructed based on estimates of connectivity of the neurons in the neural tissue.

13. The method of claim 12, wherein the connectivity between the model neurons is reconstructed based on morphological shapes of corresponding neurons in the neural tissue.

14. The method of claim 1, wherein the multiple user inputs comprise user inputs that block activity in upper layers of the neural tissue and deeper layers of the neural tissue.

15. The method of claim 1, wherein the multiple user inputs comprise user inputs that block inhibitory and excitatory connections in the neural tissue.

16. The method of claim 1, wherein the virtual volume of neural tissue comprises approximately 638±74 million appositions, 36.7±4.2 million synapses, and 8.1±0.9 million connections.

* * * * *